US00PP18097P2

(12) United States Plant Patent
Lim

(10) Patent No.: US PP18,097 P2
(45) Date of Patent: Sep. 25, 2007

(54) SHRUB ROSE PLANT NAMED 'BAICER'

(50) Latin Name: *Rosa hybrida*
Varietal Denomination: BAIcer

(75) Inventor: Peter P. Lim, McMinnville, OR (US)

(73) Assignee: Bailey Nurseries, Inc., Newport, MN (US)

( * ) Notice: Subject to any disclaimer, the term of this patent is extended or adjusted under 35 U.S.C. 154(b) by 0 days.

(21) Appl. No.: 11/408,349

(22) Filed: Apr. 21, 2006

(51) Int. Cl.
*A01H 5/00* (2006.01)

(52) U.S. Cl. ..... Plt./102

(58) Field of Classification Search ..... Plt./102
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of shrub rose, 'BAIcer', characterized by its clusters of double, ruffled, bi-colored flowers with petals that are deep red-purple on the upper surface and white blushed with pink on the lower surface. 'BAIcer' blooms abundantly in May and June and then recurrently throughout the season. The upright rounded plant habit with foliage resistant to black spot and mildew make 'BAIcer' well suited for the landscape. The new variety is readily propagated on its own roots and hardy in U.S.D.A. Zones 4 to 9.

2 Drawing Sheets

Botanical classification: *Rosa hybrida.*
Variety denomination: 'BAIcer'.

BACKGROUND OF THE INVENTION

The present invention relates to a new and distinct cultivar of *Rosa hybrida.* The new cultivar will be referred to hereafter by its cultivar name, 'BAIcer'. 'BAIcer' is a shrub rose suitable for landscape plantings.

The new cultivar of shrub rose is a selection from a controlled breeding program conducted by the inventor in Yamhill, Oreg. with a focus to create cultivars of roses with greater winter hardiness and improvements in disease resistance combined with good flower quality.

The new variety of shrub rose, 'BAIcer', designated as seedling No 96R509, was selected among seedlings derived from a cross made in Yamhill, Oreg. in 1996 between the female parent, designated R92108 (unnamed proprietary seedling, not patented) and the male parent, 'MACmanley' (U.S. Plant Pat. No. 6,907). 'BAIcer' was selected as unique and budded onto understock in August 1997 and reselected by the inventors for its distinct characteristics in 2001.

The new cultivar has been asexually propagated by budding on an understock of 'Dr. Huey' (not patented) and by rooting of softwood cuttings. Asexual propagation in Yamhill, Oreg., St. Paul, Minn. and Litchfield, Ariz. by these techniques have determined that the characteristics of this cultivar are stable and are reproduced true to type in successive generations.

SUMMARY OF THE INVENTION

The following traits have been repeatedly observed and represent the characteristics of the new rose as observed for a period of three years in Yamhill, Oreg. and St. Paul, Minn. These attributes in combination distinguish 'BAIcer' as a unique cultivar of shrub rose.

1. 'BAIcer' exhibits clusters of double, ruffled, bi-colored flowers with petals that are red purple on the upper surface and white blushed with pink on the lower surface. Classified as a pink-blend by American Rose Society standards.
2. 'BAIcer' exhibits a bushy, upright rounded plant habit.
3. 'BAIcer' is a recurrent bloomer, blooming abundantly in May and June and then recurrently throughout the season.
4. 'BAIcer' has shown excellent resistance to rose black-spot (*Diplocarpon rosae*) and powdery mildew (*Sphaerotheca pannosa* var. *rosa*).
5. 'BAIcer' forms red hips late in the growing season.
6. 'BAIcer' is hardy in U.S.D.A. Zones 4 to 9.
7. 'BAIcer' is a vigorous grower and readily propagated by softwood cuttings and grown on its own roots.

The new cultivar of shrub rose can be readily distinguished from its parents and other cultivars. The female parent, seedling No. R92108, has larger flowers with more petals and darker green foliage. The male parent, 'MACmanley', an everblooming miniature rose, has smaller red flowers with a distinct white eye colored flowers and a compact mounded habit. The cultivars 'Meipitac' (U.S. Plant Pat. No. 7,783) and 'Seven Sisters' (not patented) are the closest comparison roses. They are both similar to 'BAIcer' in having double red flowers with pink tints, however 'Meipitac' is an everblooming shrub rose with larger flowers and a compact rounded habit and 'Seven Sisters' is a June blooming climbing rose.

BRIEF DESCRIPTION OF THE DRAWING

The accompanying colored photographs illustrate the overall appearance and distinct characteristics of the new shrub rose, 'BAIcer', as grown outdoors in trial blocks and containers in St. Paul., Minn. and Yamhill, Oreg. The photographs were taken of two to three year-old plants grown on their own roots.

Figure 1:
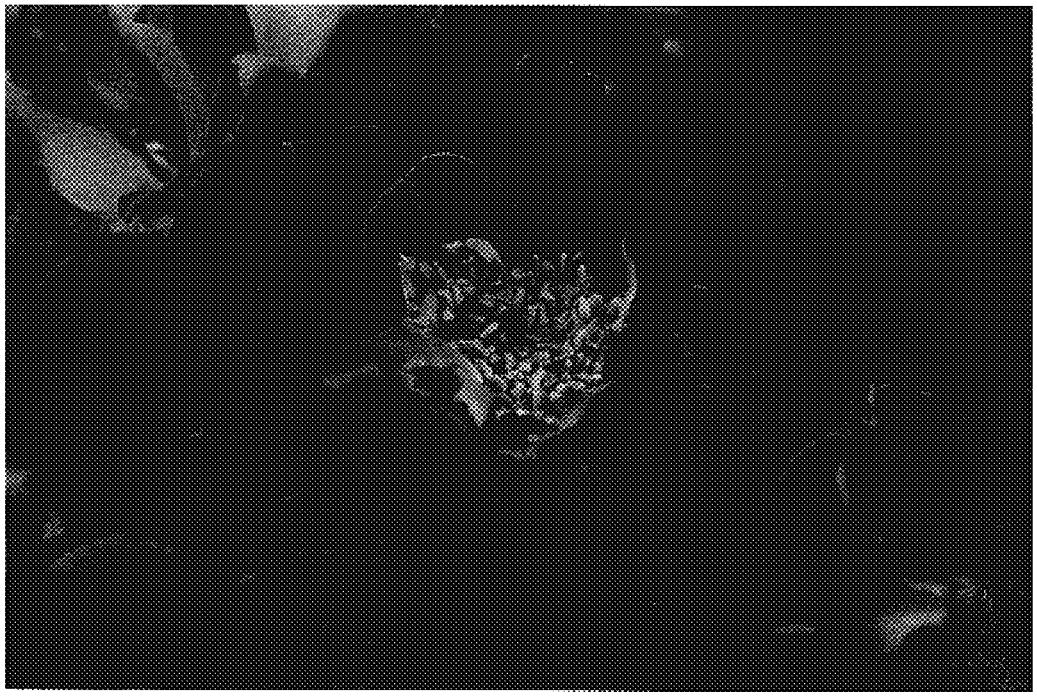
FIG. 1 illustrates a fully open flower.
Figure 2:
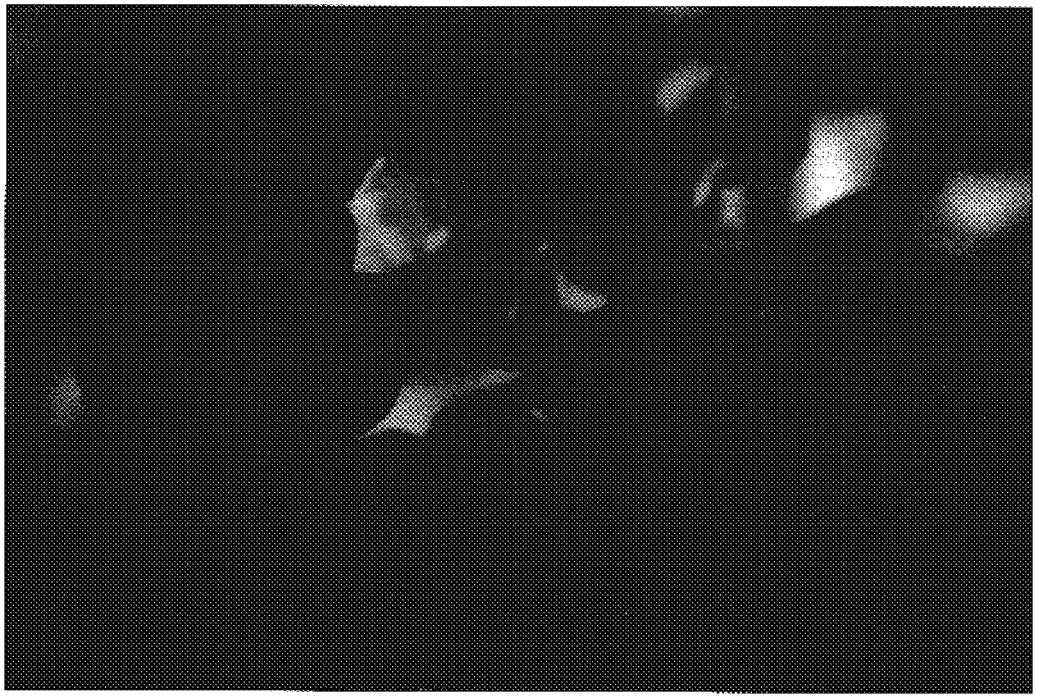
FIG. 2 provides a view of the lower side of the petals of a fully open flower, FIG. 3 provides a close-up view of an opening flower.
Figure 3:
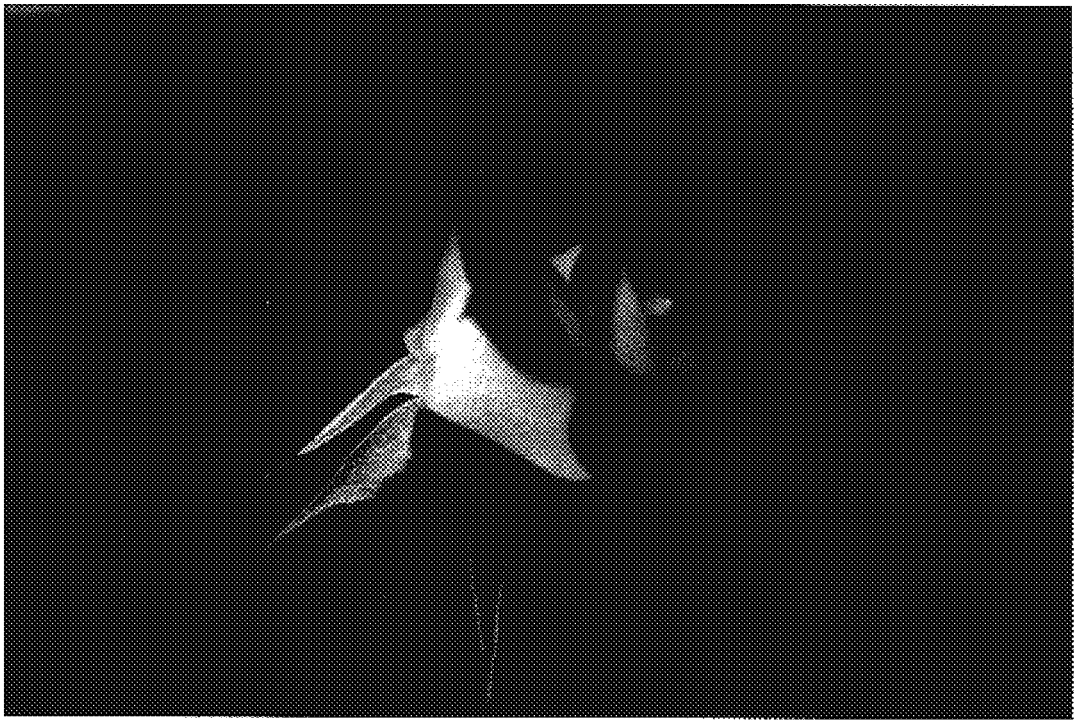
Figure 4:
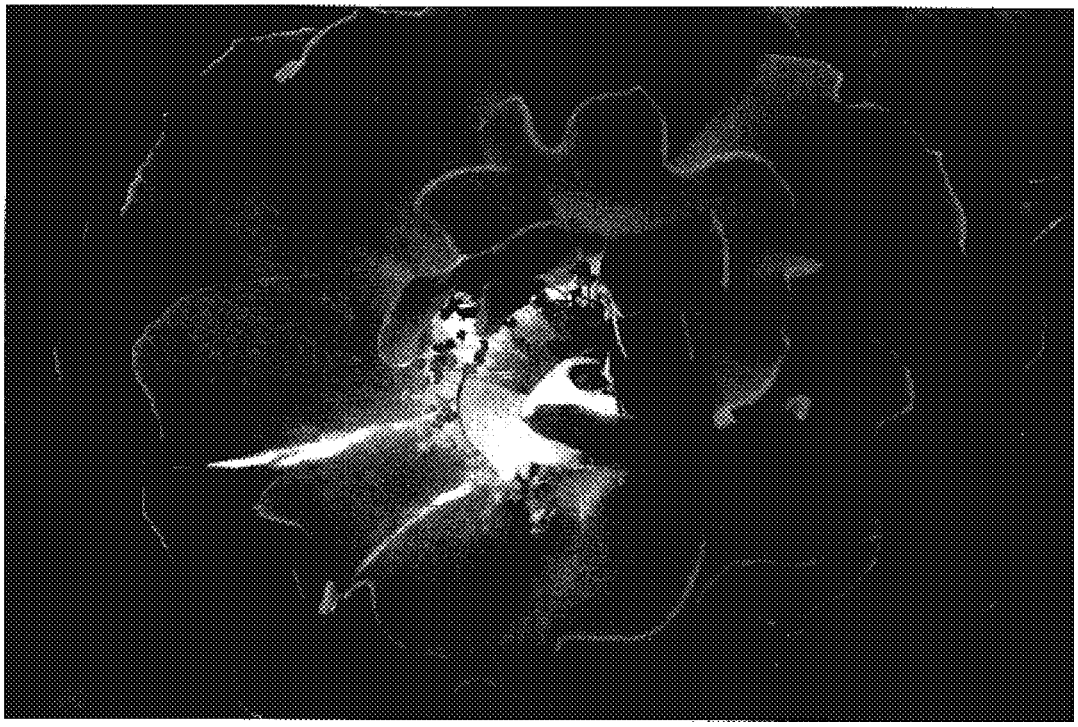
FIG. 4 illustrates the color of a maturing flower.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on two and four year-old plants grown outdoors under field conditions in Yamhill, Oreg. and St. Paul, Minn. The phenotype of the new cultivar may vary with variations in environmental, climatic, and cultural conditions, as it has not been tested under all possible environmental conditions. The color determination is in accordance with The R.H.S. Colour Chart of The Royal Horticultural Society, London, England, except where general color terms of ordinary dictionary significance are used.

General description:

*Botanical classification.*—*Rosa hybrida* 'BAIcer'.

*Parentage.*—Seed parent R92108 (proprietary unnamed shrub rose seedling), pollen parent *Rosa* 'MACmanley'.

*Blooming habit.*—Abundant in May and June and recurrent throughout the growing season.

*Plant habit.*—Bushy, upright rounded habit.

*Height and spread.*—Reaches 60 to 90 cm in height and 50 cm to 80 cm in spread.

*Cold hardiness.*—U.S.D.A. Zone 4 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young; 144A, maturing; 137A, mature wood; 137B with areas of 199A and 200D.

*Stem surface.*—Young; glabrous, adult wood; mostly glabrous with bark-like ridges.

*Thorns.*—Triangular in shape, oval base, average of 6 per 5 cm in number, average of 7.4 mm in length with a base 8.8 mm in length and 2 mm in width, color is primarily 165B with 165A toward the tip.

Foliage description:

*Leaves.*—Division is odd-pinnate, average of 8.3 cm in length and 7.8 cm in width, internode length is an average of 1.8 cm.

*Leaflets.*—Average of 5,oval to rotund in shape, rounded base, rounded to broadly acute apex, serrated margins, glabrous with satin sheen on upper surface and lower surface, average of 4.2 cm in length and 2.7 cm in width, color; young leaves upper surface; 187B suffused with 137B, young leaves lower surface; between 187A and 187B suffused with 137B, mature leaves upper surface; 147A, mature leaves lower surface; 147B.

*Rachis.*—Average of 6.3 cm in length and 1.2 mm in diameter, color of upper surface 146C with 146A on parallel ridges, color of lower surface 146C.

*Stipules.*—Parallel with auricle facing outward, average of 2.5 cm in length and 5.3 mm in width, color is 145B with upper surface of auricle 146B and 147B and lower surface of auricle a color between 146B and 146C.

*Petioles.*—Average of 2.1 cm in length and 1.75 mm in diameter, color of upper surface 146C with 146A on parallel ridges, color of lower surface 146C, glabrous surface.

Inflorescence description:

*Inflorescence type.*—Singles or corymbs of double flowers.

*Flower number.*—Average of 3 per lateral stem.

*Flower fragrance.*—Slight apple scent.

*Flower longevity.*—About 4 to 6 days, depending on temperature and sunlight exposure.

*Flower type.*—Double and informal, irregular in outline and in arrangement and size of petals.

*Flower size.*—Average of 5 cm in diameter and 2 cm in depth.

*Peduncles.*—Stiff, average of 5.9 cm in length and 2 mm in diameter, surface has small flexible spines especially dense near flower base, color is between 144A and 144B suffused with 184B on side facing the sun, color is 145C in shaded side, sparsely covered with prickles.

*Flower buds.*—Urn shaped, medium in size with an average of 2 cm in length and 1.25 cm in width prior to opening, color 4D with streaks of 51A and 53C with most petals suffused with 53D on margins.

*Sepals.*—5, broadly lanceolate in shape, margin is entire and ciliate with 3 to 4 sepals having foliaceous appendages in a pinnate pattern, color of upper surface 143A, color of lower surface 144A suffused with 185B, upper surface is tomentose, lower surface is strigose, average of 2.5 cm in length and 7 mm in width, apex is apiculate changing to a small leaf, base is blunt, aspect is upright in bud stage changing to horizontal when bud opens and reflexed in full bloom.

*Petals.*—Average of 18, drop readily and cleanly, orbicular in shape, ruffled in aspect, upper and lower surface is glabrous and satiny, entire margin, rounded base, cuspidate apex, average of 3 cm in length and 2.4 cm in width, color: opening flowers upper surface; outer petals 57A turning to 45A near petal spot at base and inner petals 45A, opening flowers lower surface; 4D with streaks of 5B, 55B and 55C and most are suffused with 53D on margin, fully open flowers upper surface; 57A fading to 57D toward base spot, fully open flowers lower surface; 155C with tint of 56A and suffused with 57A and 57C toward petal margin, end of bloom upper surface; 57C blended with 57D and 58C, end of bloom lower surface; 155C with tint of 56A and suffused with 57A and 57C toward margin and part of petal exposed to sun, base petal spot; 11D becoming 10A at base.

*Receptacle.*—Average of 6.3 mm in diameter and 9.1 mm in depth when flower is fully open, urn shaped, glabrous with some glaucous coating, color is between 143B with 183C on the side exposed to sun.

*Pistils.*—Average of 38, stigma is an average of 0.4 mm in length, an average of 0.8 mm in width and 154C in color, style is an average of 3.75 mm in length and 2B in color.

*Stamens.*—Average of 68, filaments are about 5 mm in length and 14A in color, anthers are an average of 2.3 mm in length, an average of 1.1 mm in width and 12C in color, pollen is 21B in color.

*Hips.*—Urn shaped, medium small in size with an average of 8.5 mm in length and 6 mm in diameter, surface is glabrous with some ridges, color is 176A suffused with 147B, seeds; rounded to oval in shape, an average of 5 mm in length and 4 mm in width, surface is rugose at apex with villose hairs, color is 165A with areas of 164A and 165B.

I claim:

1. A new and distinct cultivar of shrub rose plant named 'BAIcer' as herein illustrated and described.

* * * * *